(12) United States Patent
Boydens et al.

(10) Patent No.: US 11,435,188 B2
(45) Date of Patent: Sep. 6, 2022

(54) AGRICULTURAL SYSTEM

(71) Applicant: CNH Industrial America LLC, New Holland, PA (US)

(72) Inventors: Joachim Boydens, Zedelgem (BE); Thomas Debbaut, Ronsele (BE); Didier Verhaeghe, Ypres (BE); Brecht Vermeulen, Gullegem (BE)

(73) Assignee: CNH Industrial America LLC, New Holland, PA (US)

( * ) Notice: Subject to any disclaimer, the term of this patent is extended or adjusted under 35 U.S.C. 154(b) by 226 days.

(21) Appl. No.: 16/612,571

(22) PCT Filed: May 9, 2018

(86) PCT No.: PCT/EP2018/062060
§ 371 (c)(1),
(2) Date: Nov. 11, 2019

(87) PCT Pub. No.: WO2018/206673
PCT Pub. Date: Nov. 15, 2018

(65) Prior Publication Data
US 2020/0208984 A1 Jul. 2, 2020

(30) Foreign Application Priority Data

May 9, 2017 (BE) .................................. 2017/5339

(51) Int. Cl.
*G01C 21/20* (2006.01)
*G01C 21/34* (2006.01)
(Continued)

(52) U.S. Cl.
CPC ......... *G01C 21/20* (2013.01); *G01C 21/3407* (2013.01); *G01N 33/0098* (2013.01)

(58) Field of Classification Search
CPC .... G10C 21/20; G10C 21/3407; G10C 21/32; G01N 33/0098; G06Q 10/04; G06Q 50/02;
(Continued)

(56) References Cited

U.S. PATENT DOCUMENTS 5,327,820 A * 7/1994 McClure ............... A01F 15/141
100/5
5,327,821 A * 7/1994 McClure ............... A01F 15/141
100/5
(Continued)

FOREIGN PATENT DOCUMENTS

EP 1548531 A1 6/2005
EP 1 548 531 A1 * 7/2014
(Continued)

OTHER PUBLICATIONS

International Search Report and Written Opinion for Application No. PCT/EP2018/062060 dated Jun. 15, 2018 (12 pages).

*Primary Examiner* — Jeffrey P Aiello
(74) *Attorney, Agent, or Firm* — Peter Zacharias; Patrick Sheldrake (57) ABSTRACT

A system including: a controller configured to: receive bale-location-data representative of the location of a plurality of bales in a field; receive bale-property-data representative of one or more physical properties of each of the plurality of bales; and determine bale-pick-up-data based on the bale-location-data and the bale-property-data. The bale-pick-up-data is associated with an operation to pick up the bales from the field.

16 Claims, 3 Drawing Sheets

(51) Int. Cl.
*G01N 33/00* (2006.01)
*G06Q 50/02* (2012.01)

(58) Field of Classification Search
CPC ............... H04W 4/025; A01F 15/0833; A01F 2015/0891
USPC ...... 701/50; 702/19, 38, 102, 150, 152, 158, 702/182, 188
See application file for complete search history.

(56) References Cited

U.S. PATENT DOCUMENTS

| | | | | |
|---|---|---|---|---|
| 5,557,510 | A * | 9/1996 | McIntyre | ............... A01F 15/07 172/75 |
| 2012/0096827 | A1* | 4/2012 | Chaney | ............... A01F 15/106 56/341 |
| 2012/0112896 | A1* | 5/2012 | Clair | .................... A01B 69/008 340/436 |
| 2016/0235007 | A1* | 8/2016 | Hoffmann | ........... A01F 15/0833 |
| 2017/0013783 | A1* | 1/2017 | Kirk | .................... A01F 15/0883 |

FOREIGN PATENT DOCUMENTS

| | | |
|---|---|---|
| WO | 2014/137533 A2 | 9/2014 |
| WO | WO 2014137533 A2 * | 9/2014 |

\* cited by examiner

AGRICULTURAL SYSTEM

BACKGROUND OF THE INVENTION

It is known for balers to produce and deposit bales of crop material in an agricultural field. The position of the bales can be determined by the instants in time that the baler has collected enough crop material to form a complete bale. Subsequently, one or more other agricultural vehicles can enter the field to pick up the bales and transport them out of the field, for example for storage.

SUMMARY OF THE INVENTION

According to a first aspect of the invention, there is provided a system comprising:
a controller configured to:
receive bale-location-data representative of the location of a plurality of bales in a field;
receive bale-property-data representative of one or more physical properties of each of the plurality of bales; and
determine bale-pick-up-data based on the bale-location-data and the bale-property-data, wherein the bale-pick-up-data is associated with an operation to pick up the bales from the field.

The bale-property-data may comprise one or more of: bale-dimension-data, which is representative of the physical size and/or shape of a bale; bale-density-data, which is representative of the density of crop material in the bale; bale-weight-data, which is representative of the weight of the bale; bale-quality-data, which is representative of a quality-score of the bale; bale-moisture-data, which is representative of a moisture-level of the bale; bale-crop-type-data, which is representative of the type of crop that is included in the bale; bale-temperature-data, which is representative of the temperature of the bale; bale-stalk-length-data, which is representative of the length of crop stalks in the bale; bale-time-data, which is representative of one or both of a start and end timestamp of creation of the bale; and bale-production-data, which is representative of one or more production parameters used for producing the bale.

The bale-pick-up-data may comprise pick-up-route-plan-data that is representative of the order in which the bales should be picked up. The pick-up-route-plan-data may comprise an ordered sequence of bale-pick-up-locations that correspond to the locations of the plurality bales in the field. The controller may be configured to determine the ordered sequence based on the bale-property-data.

The bale-property-data may comprise bale-quality-data. The controller may be configured to determine the ordered sequence based on an order list of the bales from high quality to low quality.

The bale-pick-up-data may comprise bale-arrangement-data, which is representative of how the bales should be arranged when they are picked up. The controller may be configured to determine the bale-arrangement-data such that bales with associated bale-property-data are positioned adjacent to each other.

The bale-arrangement-data may comprise: for each of the plurality of bales: trailer-position-data, which is representative of a position for the bale on a trailer. The controller may be configured to determine the trailer-position-data such that bales with predetermined properties are positioned in predetermined positions in the trailer.

The controller may be configured to apply one or more trailer-position-criteria to the bale-property-data in order to determine the bale-arrangement-data.

There may be provided a computer program, which when run on a computer, causes the computer to configure any apparatus, including a controller, processor, machine, vehicle or device disclosed herein or perform any method disclosed herein. The computer program may be a software implementation, and the computer may be considered as any appropriate hardware, including a digital signal processor, a microcontroller, and an implementation in read only memory (ROM), erasable programmable read only memory (EPROM) or electronically erasable programmable read only memory (EEPROM), as non-limiting examples.

The computer program may be provided on a computer readable medium, which may be a physical computer readable medium such as a disc or a memory device, or may be embodied as a transient signal. Such a transient signal may be a network download, including an internet download.

BRIEF DESCRIPTION OF THE DRAWINGS

Embodiments of the present invention will now be described by way of example and with reference to the accompanying drawings in which.

DETAILED DESCRIPTION OF THE DRAWINGS

Figure 1:
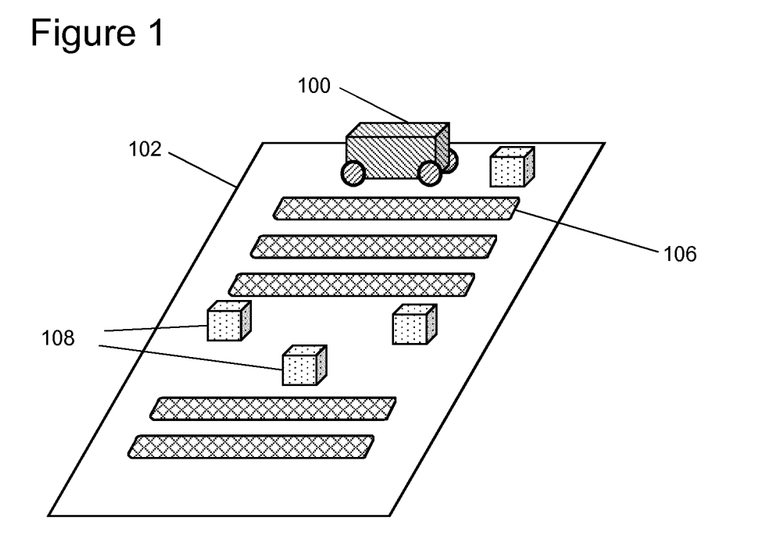
FIG. 1 shows an example of an agricultural field.
Figure 2:
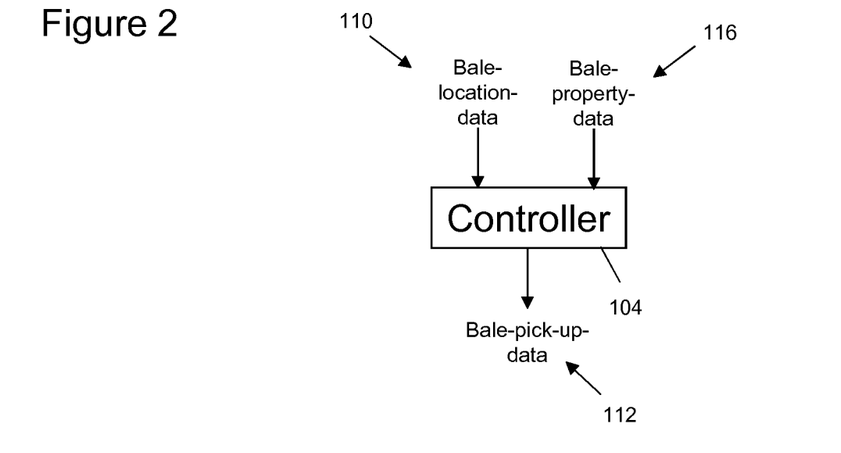
FIG. 2 shows schematically a controller for determining bale-pick-up-data that is associated with an operation to pick up bales from the field.

FIG. 2 shows schematically a system, which includes a controller 104 for determining bale-pick-up-data 112. The bale-pick-up-data 112 is associated with an operation to pick up/collect bales 108 from an agricultural field 102, as shown in FIG. 1. As will be discussed in detail below, the controller 104 can be located on a baler 100, or remotely from a baler 100. For example, the functionality of the controller 104 can be performed on a remote server, such as one "in the cloud".

The field 102 shown in FIG. 1 includes rows of crop material, which may be hay, straw or similar products that have been left in the field 102 in the form of swaths 106. The swaths 106 are elongate rows of the products in question that are heaped in the transverse centre and tend to flatten at the respective transverse edges. Typically a field 102 that has undergone harvesting contains many, essentially mutually parallel, swaths 106, as shown in FIG. 1. The swaths are spaced from one another by largely consistent gaps. The crop material in the swaths 106 can be picked up by the baler 100, and then deposited in the field 102 as bales 108. The field 102 that is shown in FIG. 1 has been partly processed, in that it includes both rows of swath 106 for baling, and also completed bales 108. It will be appreciated that more than one baler 100 may be working in the same field 102 simultaneously.

The controller 104 receives bale-location-data 110 that is representative of the location of a plurality of bales 108 in the agricultural field 102. The bale-location-data 110 can include a plurality of sets of bale-coordinates, such as GPS coordinates, with a bale-identifier associated with each set of bale-coordinates. The controller 104 also receives bale-property-data 116. The bale-property-data 116 can include one or more bale-property-values associated with each bale-identifier. Alternatively, the bale-location-data 110 and the bale-property-data 116 can be provided together such that a separate bale-identifier is not required.

The bale-property-values are representative of a physical property of a bale 108. As will be discussed below, examples of such properties include: size, weight, density, and moisture. The controller 104 determines bale-pick-up-data 112 based on the bale-location-data 110 and the bale-property-data 116. The bale-pick-up-data 112 is associated with an operation to pick up the bales 108 from the field 102. As will be discussed below, the bale-pick-up-data can include pick-up-route-plan-data (that is representative of the order in which the bales should be picked up) and/or bale-arrangement-data (that is representative of how the bales should be arranged when they are picked up, for example how they are arranged on a trailer).

Advantageously, the controller 104 can utilise the bale-property-data 116 such that the operation to pick up the bales 108 can be performed in an improved way, for example in terms of one or more of efficiency, safety, and preserving the quality of the bales.

Examples of different types of bale-property-data include:
- bale-dimension-data, which is representative of the physical size and/or shape of a bale 108. The bale-dimension-data can include one or more of: bale-length-data, bale-width-data, bale-height-data. Each of these properties can be provided as an average, maximum or minimum value (such as maximum-bale-length). The bale-dimension-data can also be implemented as bale-volume-data or bale-cross-sectional-area-data. The bale-cross-sectional-area-data can be along a cross-section that is parallel with one or more of the length, height or depth of the bale 108.
- bale-density-data, which is representative of the density of crop material in the bale 108.
- bale-weight-data, which is representative of the weight of the bale 108.
- bale-moisture-data, which is representative of a moisture-level of the bale 108.
- bale-crop-type-data, which is representative of the type of crop that is included in the bale 108.
- bale-temperature-data, which is representative of the temperature of the bale 108.
- bale-stalk-length-data, which is representative of the length of crop stalks in the bale 108.
- bale-time-data, which is representative of one or both of a start and end timestamp of creation of the bale 108.
- bale-production-data, which is representative of one or more production parameters used for producing the bale 108, such as baler chassis number, density setting, number of slices, driving speed, cutting knives engaged or not, etc.
- bale-quality-data, which is representative of a quality-score of the bale 108. In some examples, the controller 104 can compare: (i) values for one or more of the bale-property-data disclosed herein; with (ii) one or more target-values/parameter-thresholds, and then the controller 104 can set the bale-quality-data based on the results of the comparison. In some examples, the parameter-thresholds can be crop dependant—for instance it may be desirable for the humidity for wheat straw bales to be a lot less than the humidity of grass bales. In some examples, the target-values/parameter-thresholds can be set based on user-input such that they are dependent on a user's particular preferences. For instance, a user desires bales of 450 kg and 2.4 m long, then these can be used as the target-values. A user may be able to provide input that is representative of a target-value or target-range for one or more of: weight, length and humidity. The controller 104 can then determine a quality-score based on the deviation from these, or any other, parameters.

It will be appreciated that the controller 104 can calculate some of the above types of bale-property-data based on other types of received bale-property-data. For instance, the controller 104 could divide the bale-weight-data by the bale-volume-data in order to determine bale-density-data.

In some examples the bale-pick-up-data 112 includes pick-up-route-plan-data, which is representative of the order in which the bales 108 should be picked up. In this way, the pick-up-route-plan-data can include an ordered sequence of bale-pick-up-locations that correspond to the locations of the plurality bales in the field. That is, the controller 104 can make an ordered list of the bale-coordinates that are received as the bale-location-data, based on the bale-property-data 116.

Optionally, the controller 104 can determine the ordered sequence based on bale-dimension-data for each of the bales 108. For instance, the ordered sequence can include bale-pick-up-locations for bales 108 with an increasing or decreasing size. In some applications, it can be advantageous to load the bigger bales before the smaller bales.

Optionally, the controller 104 can determine the ordered sequence based on bale-density-data/bale-weight-data for each of the bales 108. For instance, the ordered sequence can include bale-pick-up-locations for bales 108 with a decreasing density/weight. In some applications, it can be advantageous to load the more dense/heavier bales before the less dense/lighter bales, especially if the bales are going to be stacked on top of each other in a trailer, in order to reduce the likelihood that a more dense/heavier bale will be positioned on top of a less dense/lighter bale and potentially damage the less dense/lighter bale.

Optionally, the controller 104 can determine the ordered sequence based on bale-moisture-data for each of the bales 108. For instance, the ordered sequence can include bale-pick-up-locations for increasing or decreasing moisture-levels of the bales 108. In some examples, the ordered sequence can include bale-pick-up-locations for increasing moisture-levels of the bales 108, on the basis that the driest bales will probably have the highest quality. For example, if it starts to rain, then the best bales have already been brought to 'safety'.

Optionally, the controller 104 can determine the ordered sequence based on bale-crop-type-data for each of the bales 108. For instance, the ordered sequence can include bale-pick-up-locations such that all bales 108 with the same type of crop are picked up consecutively. In this way, bales having a first type of crop are picked up before bales having a second crop type, etc.

Optionally, the controller 104 can determine the ordered sequence based on bale-quality-data for each of the bales 108. For instance, the ordered sequence can include bale-pick-up-locations for increasing quality-scores from low to high, or decreasing quality-scores from high to low. In some applications, it can be advantageous to pick up high quality bales 108 first for the same reasons outlined above.

It will be appreciated that in examples where the bale-property-data 116 includes more than one type of property data, the controller 104 can apply an algorithm to the various bale-property-values and/or different types of bale-property-data in order to determine the ordered sequence. This can involve applying a predetermined hierarchy to the different types of property data, such as to order the pick up locations based on type of crop, and then quality-score. In some applications, determining the ordered sequence can involve applying predetermined weighting-values to the different types of property data/values of the bale-property-data 116. Furthermore, as will be discussed below, one or more other types of data can be taken into account by the controller 104 when determining the ordered sequence, such as fuel consumption required to travel between the pick-up locations in the ordered sequence.

In addition to determining the pick-up-route-plan-data based on the bale-property-data 116 as discussed above, the controller can also determine the pick-up-route-plan-data based on one or more other types of data. For example, based on fuel consumption required to travel between the pick-up locations in the ordered sequence instance and/or the time that will be required to follow the route. In this way, the controller 104 can determine the route such that it provides one or more advantages, for example:

(i) efficient loading/pick-up, such as low overall fuel consumption of the vehicles that are used to pick up the bales 108; and (ii) efficient loading in terms of the time required to collect all of the bales 108 from the field 102.

The pick-up-route-plan-data 112 can be representative of a route to be taken by one or more agricultural vehicles for collecting the bales and transporting them out of the field 102. For example, a first tractor to tow a trailer for receiving the bales and transporting them out of the field 102, and a second tractor with a loader/spears for picking up and moving a bale 108 onto the trailer. The pick-up-route-plan-data 112 can be provided as instructions for operators of the tractors to follow when they are in the field 102 collecting the bales. Optionally, a controller associated with the first and second tractors can provide real-time instructions to the operators of the tractors, based on their current and/or past locations, such that, by following the real-time instructions, they can follow a route to pick up the bales 108 in a desired order.

In examples where an operator drives an agricultural vehicle to follow a route that is represented by the pick-up-route-plan-data 112, a display or other output device can be used to provide instructions to the operator that are based on the pick-up-route-plan-data 112. For example, the controller 104 can generate and display an augmented reality, to indicate which bale to pick up next.

A route can be determined based on a variety of strategies, such as:
- a loader vehicle and trailer vehicle staying together.
- a loader vehicle pulling a trailer and dropping it off at certain positions.
- a loader vehicle and a trailer vehicle that stop at certain locations.
- a loader vehicle gathers bales at certain buffer locations, then loads them onto a trailer when it arrives.
- any of the above with multiple loaders and/or trailers.
- any of the above where the loader picks up multiple bales stacked onto each other before placing them in the trailer or buffer.

In such examples, a route can be planned/selected which results in a good cost-function, which is applied for evaluating different pick-up-routes. Any known optimization algorithm can be used, or adapted, in this regard. For example, if a travelled distance is to be minimised when a loader and a trailer are moving together, then the controller can apply a 'Shortest Path Problem'.

In some examples, the controller 104 can determine vehicle-control-instructions for the tractors (or any other agricultural vehicle/loader) based on the pick-up-route-plan-data 112. The vehicle-control-instructions may comprise vehicle-steering-instructions for automatically controlling the direction of travel of the tractors. The vehicle-control-instructions may further comprise route-speed-instructions for automatically controlling the speed of the tractors at locations along the route. In this way, the tractors can be autonomously controlled such that they follows a specific route through the agricultural field in order to pick up the bales 108 from the field 102.

In some examples, the bale-pick-up-data 112 can include bale-arrangement-data that is representative of how the bales should be arranged when they are picked up.

For instance, a tractor (or other agricultural vehicle) can pick up the bales 108 and place them on a trailer such that they can be transported out of the field 102. The bale-arrangement-data can include trailer-position-data, which is representative of a position for each bale 108 on the trailer. The position could an identifier of a row, column and/or height-position on the trailer, if the bales are to be arranged in this way. The position could be a specific bale-position-identifier on the trailer. The position could be a predetermined position with reference to features of the trailer such as: adjacent an edge of the trailer, in a centre region of the trailer, in a front region of the trailer, in a back region of the trailer, over an axle of the trailer, and not over an axle of the trailer.

The controller 104 can determine the trailer-position-data such that bales 108 with predetermined properties are positioned in predetermined positions in the trailer.

The bale-arrangement-data/trailer-position-data can be determined such that bales with associated bale-property-data are positioned in a predetermined relationship with each other, such as adjacent to each other. Further example details are provided below.

The controller 104 can be configured to apply one or more trailer-position-criteria to the bale-property-data 116 in order to determine the bale-arrangement-data.

Optionally, applying the trailer-position-criteria can include determining a predetermined-number of bales that have the highest/lowest bale-property-value, and determining bale-arrangement-data that corresponds to those bales being positioned at a predetermined location on the trailer.

For instance, if four bales 108 are expected to be positioned side-by-side across the width of the trailer, then the trailer-position-criteria may determine the four heaviest bales (based on bale-weight-data) in the field, and the bale-arrangement-data can be representative of those four heaviest bales being located above an axle of the trailer.

As another example, the trailer-position-criteria can include determining a predetermined number of bales that have the highest bale-quality-data, and determining trailer-position-data that is representative of those bales being furthest from a bale loading position of the trailer. In this way, an operator for loading the bales may load the highest quality bales first.

Optionally, applying the trailer-position-criteria can include determining bales that have a bale-property-value that satisfies a bale-threshold-value. The bale-threshold-value may be a maximum value, a minimum value, or a range of values. The controller 104 can then determine bale-arrangement-data that corresponds to those bales being positioned at a predetermined position on the trailer.

For instance, applying the trailer-position-criteria can include determining bales that have bale-weight-data that is greater than a bale-weight-threshold value, and determining bale-arrangement-data that corresponds to those bales being positioned at a predetermined position on the trailer, such as over or near an axle of the trailer.

As another example, applying the trailer-position-criteria can include determining bales that have bale-weight-data that is greater than a bale-weight-threshold value, and then positioning those bales at minimum distances to a position on the trailer that corresponds to an axle.

As another example, applying the trailer-position-criteria can include processing the bale-moisture-data such that bales with similar moisture-levels are positioned adjacent to each other on the trailer. For instance, all bales with a moisture-level that is within a predetermined range of moisture levels can be positioned adjacent to each other. This can result in the wettest bales being positioned all together, and therefore can reduce the likelihood of 'wet' bales transferring moisture to other 'dry' bales. Also, by placing bales with similar moisture levels next to each other, it can be easier to filter out bales with specific moisture levels when they arrive at a storage location.

In some examples, the controller 104 can determine pick-up-route-plan-data based on the bale-arrangement-data. For instance, the controller 104 can determine a layout of the bales on the trailer, and then the controller 104 can determine an ordered sequence for picking up the bales 108 that is consistent with the layout. This may involve picking up bales that are to be placed at a least accessible position on the trailer before bales that that are to be placed at a more accessible position. In examples where the bales are going to be stacked on top of each other on the trailer (in which case the bale-arrangement-data can be representative of a three-dimensional layout of the bales), the controller 104 may determine the pick-up-route-plan-data such that bales are picked up based on the layer in which they are to be placed, from bottom to top. Or at least such that any lower bales that are required to support a higher bale are loaded first.

In other examples, the bale-arrangement-data can be presented to an operator of an agricultural vehicle (such as a loader) when collecting the bales 108 from the field 102, such that the operator can arrange the bales 108 in a desired way. Optionally, a controller associated with the agricultural vehicle can provide real-time instructions to the operator of the agricultural vehicle, based on their current and/or past locations, such that, by following the real-time instructions, they can arrange the bales 108 in an advantageous way.

Figure 3:
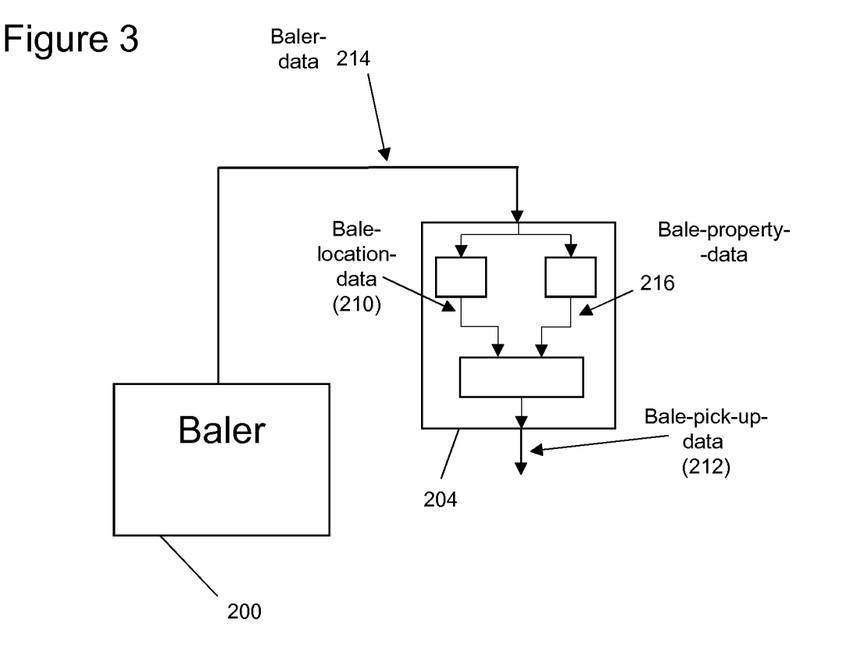
FIG. 3 shows schematically another controller for determining bale-pick-up-data.

FIG. 3 shows schematically another system for determining bale-pick-up-data 212. The system includes a controller 204 and a baler 200. The baler 200 provides baler-data 214 to the controller 204. As will be discussed below, the controller 204 can then determine bale-location-data 210 and/or bale-property-data 216 based on the baler-data 214. It will be appreciated that the controller 204 may or may not be located locally with the baler 200. In some examples, the baler 200 can provide the baler-data 214 to a remote controller 204 via a telematics system and can use an internet connection. Alternatively, the controller 204 can be in wired communication with the necessary components of the baler 200.

In examples where multiple balers process a field, each of the balers can provide baler-data to the controller 204. For instance, inter-vehicle communication can be used if there is more than one baler working on the field. This communication can be direct or indirect, such as through "the cloud".

As will be appreciated from the following description, the baler 200 can send one or more of the estimated location, orientation, dimensions and drop time of bales that have been dropped.

The baler-data 214 can include baler-location-data representative of the location of the baler 200 at instants in time that the baler 200 deposits bales in the field. Such information may be stored, and made available, each time the baler 200 deposits a bale. The controller 204 can determine the bale-location-data 210 as a single set of coordinates for each bale. The single set of coordinates may be representative of the location of the expected centre of the bale, for example, and could be calculated by the controller 204 applying an offset to the location of the baler 200 (as determined from the baler-location-data) when the bale was dropped. The offset can be indicative of a distance between: (i) a location-determining-module (such as a GPS receiver) that is fitted to the baler 200; and (ii) an exit point of the baler 200 from which the bale is dropped. The controller 204 can apply the offset to the location of the baler 200 in a direction that is opposite to the direction of travel of the baler 200 when the bale was dropped. The controller can also use the ground-speed of the baler to make corrections to the location of the bale drop.

In some examples, the baler-data 214 may include bale-dimension-data, which is an example of bale-property-data 216 that is representative of the size and/or shape of the bale. The bale-dimension-data, such as the bale-cross-sectional-area-data, may be fixed/hard-coded for a specific baler, or it may be determined using one or more sensors that measures the dimensions of each individual bale that is produced. In such examples, the controller 204 can determine the bale-location-data 210 as multiple sets of coordinates for each bale. The multiple sets of coordinates may be representative of the locations of one or more corners of the bale, for example, and may be sufficient such that, together, they can be used to determine the perimeter of a two-dimensional footprint of the bale (such as when viewed from above), or to determine the perimeter of the three-dimensional volume of the bale.

The controller 204 can determine the multiple sets of coordinates by applying offsets to the location of the baler (baler-location-data) when the bale was dropped. The controller 204 can determine the offsets based on the bale-dimension-data. Optionally, the controller 204 can also determine the offsets based on a distance between: (i) a location-determining-module that is fitted to the baler 200; and (ii) an exit point of the baler 200 from which the bale is dropped.

In some examples, the baler-data 214 can include length-wheel-data (data from a starwheel in a bale chamber of the baler 200). The length-wheel-data is representative of the thickness of a slice of crop in the bale. The controller 204 can use the length-wheel-data to determine bale-dimension-data.

In some examples, the baler-data 214 can include stuffer-data, which is representative of a number of slices of crop material that are included in a bale. A stuffer trip sensor on the baler 200 can provide the stuffer-data. The controller 204 can use the stuffer-data to determine bale-dimension-data.

In some examples, the baler-data 214 can include knotter-data, which is representative of instants in time when the baler has completed a bale, and started to form a new bale. A knotter signal indicate the start and end of a bale. So, by summing displacement-values that are measured by a starwheel between 2 knotter signals, the controller 204 can determine the total length of the bale. Also, when the end of the bale is knotted, the controller 204 can determine where the bale is in the bale chamber and its dimensions. Therefore, the controller 204 can start tracking the movement of this bale in the bale chamber. The controller 204 can therefore also determine when the bale is leaving the bale chamber and if the controller 204 also receives a bale-drop signal, the controller 204 can determine that it is that bale that is falling off the machine. In this way, knotter-data can be used to determine bale-dimension-data and or bale-location-data.

In some examples, the baler-data 214 can include bale-weight-data that is acquired by a weight-sensor (not shown) that measures the weight of a bale when it is formed. For example, the weight sensor can be associated with a bale chute of the baler 200.

In some examples, the baler-data 214 may include bale-density-data, which is based on a density-setting received from the baler 200. The density-setting can be set by an operator of the baler to control the intended crop density in the bale 108. Alternatively, the controller 204 can divide bale-weight-data by bale-volume-data, which can be determined form the baler-data 214.

In some examples, the baler-data 214 can include bale-crop-type-data. For example, the baler 200 may have a user interface, that an operator of the baler 200 can use to select the type of crop that is being baled.

In some examples, the baler-data 214 can include bale-moisture-data that is acquired by a humidity sensor kit associated with the baler 200.

The controller 204 can then determine the bale-pick-up-data 212 based on the bale-location-data 210 and/or the bale-property-data 216 that was calculated using the baler-data 214.

Figure 4:
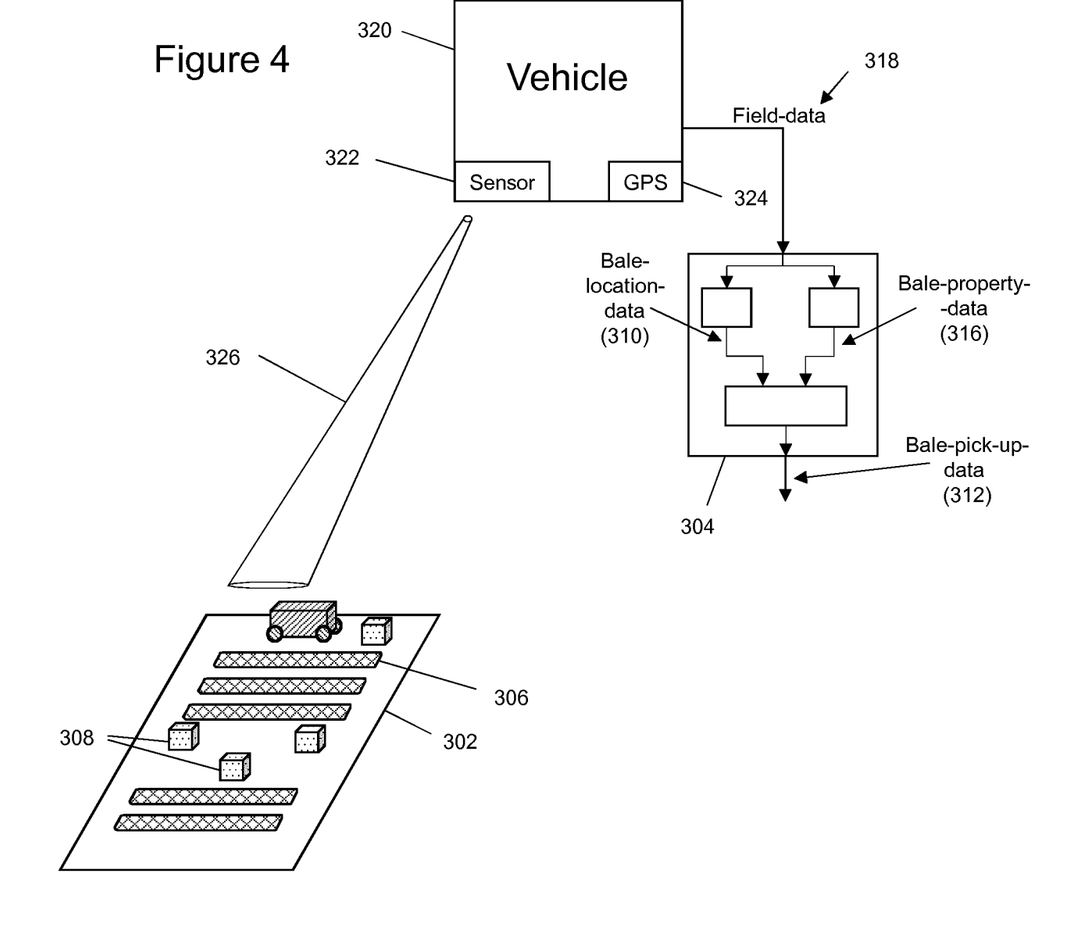
FIG. 4 shows schematically a further still controller for determining bale-pick-up-data.

FIG. 4 shows schematically another system for determining bale-pick-up-data 312. Features of FIG. 4 that are also shown in FIG. 2 or FIG. 3 have been given corresponding reference numbers in the 300 series, and will not necessarily be described again here.

The system includes a vehicle 320. In this example the vehicle is an unmanned vehicle 320. The unmanned vehicle 320 can be an unmanned aerial vehicle (sometimes referred to as a drone). In other examples, the vehicle 320 could be a land vehicle, which may or may not be unmanned.

The unmanned vehicle 320 can include one or more sensors for obtaining field-data 318, and a field of view 326 of such a sensor is shown schematically in FIG. 4. Field-data 318 that is representative of the unprocessed swath 306 and or the bales 308 can be processed in order to determine bale-property-data 316. For instance, properties of the swath 302 that are not expected to significantly change when it is baled, can be used as bale-property-data. An example of such a property is bale-crop-type-data.

In this example, the unmanned vehicle 320 includes a sensor 322 that can acquire field-data 318. In this example the sensor 322 is a camera that can acquire field-image-data. The field-image-data can be two-dimensional-image-data or three-dimensional-image-data, and in some examples the camera can be a 3D-scanner or 3D-camera.

Alternatively, or additionally, the field-data 318 can include: field-radar-data acquired by a radar, field-LIDAR-data acquired by a LIDAR sensor; field-moisture-data acquired by a moisture-sensor, field-IR-data acquired by an infra-red-sensor, ultrasonic-data acquired by an ultrasonic sensor, or any other type of field-data 318 from any type of sensor that can acquire information about the agricultural field 302 or the crop material in the agricultural field 302. The controller 304 can process one or more of these different types of field-data 318, either directly or indirectly, in order to determine one or both of the bale-location-data 310 and the bale-property-data 316.

The controller 304 can determine the bale-property-data based (directly or indirectly) on the field-data 318. For instance, the controller 304 can process the field-data 318 in order to determine bale-crop-type-data. The controller 304 can perform an object recognition algorithm on the field-image-data (data that is representative of the swath 302 and/or a bale 308) in order to determine one or more of: crop-type (bale-crop-type-data), and length of stalks in the material (bale-stalk-length-data).

In some examples, the controller 304 can also, or instead, process different types of field-data 318 to determine the bale-property-data 316. For instance, the controller 304 can process field-IR-data to determine the temperature of crop material (bale-temperature-data), or the controller 304 can process field-moisture-data to determine the humidity/wetness of crop material (bale-moisture-data).

In one example, the controller 304 can determine bale-dimension-data based on the field-data 318. The bale-dimension-data can include the height, width, cross-sectional area, volume, or shape of the bales 308. The bale-dimension-data can therefore represent one-dimensional, two-dimensional or three-dimensional physical characteristics of the bales 308, and can be determined based on two-dimensional-image-data or three-dimensional-image-data.

The controller 304 can determine field-property-data that is representative of a property of the agricultural field 302, based on the field-data 318. The field-property-data can include field-contour-data that is representative of contours of the agricultural field 302. A user can provide the field-contour-data to the controller 304 in some examples because this data acquisition can be considered as a one-time job. In other examples, the controller 304 can determine the field-contour-data based on the field-image-data or field-radar-data, for example. The controller 304 can then determine pick-up-route-plan-data, as an example of bale-pick-up-data 312, based on the field-contour-data.

In some examples, the vehicle 320 can include a height-measurement-sensor for acquiring bale-height-data representative of the height of the bales 308. If multiple height measurements are taken whilst the vehicle 320 is moving, they can be combined in order to provide a 3D-scan of a bale 308. The height-measurement-sensor can also be used to measure stub-height-information, which is representative of stub height, if the stub density is high enough. Irrespective of how the stub height is determined, in some examples the controller 304 can subtract the stub height from the measured height of the bale in order to determine bale-height-data.

The vehicle 320 can acquire: (i) field-data 318 that is representative of the agricultural field 302 that has one or more bales 308 located in it; and (ii) field-location-data (not shown) associated with the field-data 318. The controller 304 can optionally determine the bale-pick-up-data 312 based on the field-data 318 and the field-location-data.

In this example, the vehicle 320 acquires field-location-data associated with field-image-data. For example, the vehicle 320 may have a location-determining-system 324, such as GPS, that provides vehicle-location-data that is representative of the location of the vehicle 320 when the field-image-data is acquired. The controller 304 may also receive camera-direction-data and vehicle-altitude-data. The camera-direction-data may be representative of the direction that the camera is facing relative to the vehicle 320. The camera-direction-data may be hard coded if the camera is non-movably fixed to the vehicle 320. If the camera is movably mounted to the vehicle 320, then the camera-direction-data can take different values, which may be received as an input-signal at the controller 304 from the vehicle 320. The controller 304 can then use a simple trigonometric algorithm to attribute field-location-data to objects/areas that are represented by the field-image-data based on the vehicle-location-data, the camera-direction-data, a vehicle-altitude-data (if the vehicle 320 is an aerial vehicle), and a direction of travel of the vehicle 320, as is known in the art.

Also, in this example, the controller 304 determines the bale-location-data 310 based on the field-data 318 and the field-location-data. The controller 304 can also determine bale-dimension-data that is representative of the size of the one or more bales, based on the field-data 318 and/or the field-location-data. As discussed above, the controller 304 can then determine the bale-location-data 310 also based on the bale-dimension-data.

Use of an aerial vehicle 320 can enable field-data 318 to be acquired from a relatively high altitude to obtain an overview of the field 302, thereby providing a wide field of view. During baling, another strategy can be used: the aerial vehicle 320 can fly behind a baler to record data so that the controller 304 can determine the bale-location-data 310 and/or bale-property-data 316 as the bales 308 are deposited onto the field 302.

It will be appreciated that one or more of the functions of the vehicle 320 that are described with reference to FIG. 4 could be implemented by the agricultural vehicle/baler 300 itself in some examples. For example, field-data 318 as it described above could be determined by processing signals acquired by sensors on the agricultural vehicle/baler 300.

Also, in some examples, a controller can use a combination of baler-data received from a baler and field-data received from one or more sensors to determine the bale-location-data and the bale-property-data. The baler-data and the field-data can be used together, for example as part of a single algorithm or determine different types of bale-property-data. Alternatively, the controller can use the baler-data to determine bale-location-data, and can use the field-data to determine the bale-property-data, or vice versa.

The invention claimed is:

1. A system comprising:
   a controller carrying out an agricultural method, the method including the steps of:
      receiving bale-location-data representative of a location of a plurality of bales in a field;
      receiving bale-property-data representative of one or more physical properties of each of the plurality of bales;
      determining bale-pick-up-data based on the bale-location-data and the bale-property-data; and
      deriving bale-arrangement-data and including the bale-arrangement-data in the bale-pick-up-data,
   wherein the bale-pick-up-data is utilized in an operation that picks up the bales from the field, and the bale-arrangement-data is representative of how the bales should be arranged when each bale is picked up.

2. The system of claim 1, wherein the bale-property-data comprises bale-dimension-data, which is representative of a physical size or shape of the each bale.

3. The system of claim 1, wherein the bale-property-data comprises bale-density-data, which is representative of a density of crop material in the each bale.

4. The system of claim 1, wherein the bale-property-data comprises bale-weight-data, which is representative of a weight of the each bale.

5. The system of claim 1, wherein the bale-property-data comprises bale-quality-data, which is representative of a quality-score of the each bale.

6. The system of claim 1, wherein the bale-property-data comprises one or more of:
   bale-moisture-data, which is representative of a moisture-level of the each bale;
   bale-crop-type-data, which is representative of a type of crop that is included in the each bale;
   bale-temperature-data, which is representative of a temperature of the each bale;
   bale-stalk-length-data, which is representative of a length of crop stalks in the each bale;
   bale-time-data, which is representative of one or both of a start and end timestamp of creation of the each bale; and
   bale-production-data, which is representative of one or more production parameters used for producing the each bale.

7. The system of claim 1, wherein the bale-pick-up-data comprises pick-up-route-plan-data that is representative of an order in which the bales should be picked up.

8. The system of claim 7, wherein the pick-up-route-plan-data comprises an ordered sequence of bale-pick-up-locations that correspond to locations of the plurality bales in the field.

9. The system of claim 8, wherein the controller is configured to determine the ordered sequence based on the bale-property-data.

10. The system of claim 9, wherein the bale-property-data comprises bale-quality-data, and wherein the controller is configured to determine the ordered sequence based on an order list of the bales from high quality to low quality.

11. The system of claim 1, wherein the bale-pick-up-data comprises bale-arrangement-data, which is representative of how the bales should be arranged when they are picked up.

12. The system of claim 11, wherein the controller is configured to determine the bale-arrangement-data such that bales with associated bale-property-data are positioned adjacent to each other.

13. The system of claim 11, wherein the bale-arrangement-data comprises:
   for each of the plurality of bales: trailer-position-data, which is representative of a position for the each bale on a trailer.

14. The system of claim 13, wherein the controller is configured to determine the trailer-position-data such that bales with predetermined properties are positioned in predetermined positions on the trailer.

15. The system of claim 14, wherein the controller is configured to apply one or more trailer-position-criteria to the bale-property-data in order to determine the bale-arrangement-data.

16. An agricultural method carried out by and agricultural system, the method comprising the steps of:
   receiving bale-location-data representative of a location of a plurality of bales in a field by a controller of the system;
   receiving bale-property-data representative of one or more physical properties of each of the plurality of bales by the controller;
   determining bale-pick-up-data based on the bale-location-data and the bale-property-data; and deriving bale-arrangement-data and including the bale-arrangement-data in the bale-pick-up-data, picking up the bales in the field dependent upon the bale-pick-up-data, and the bale-arrangement-data is representative of how the bales should be arranged when each bale is picked up based upon the bale-property-data.

* * * * *